United States Patent [19]

Nicholson

[11] Patent Number: 5,607,299
[45] Date of Patent: Mar. 4, 1997

[54] ORTHODONTIC BRACKETS

[76] Inventor: James A. Nicholson, 120 S. 28th Ave., Hattiesburg, Miss. 39401

[21] Appl. No.: 435,272
[22] Filed: May 5, 1995

Related U.S. Application Data

[63] Continuation of Ser. No. 172,236, Dec. 23, 1993, abandoned.

[51] Int. Cl.⁶ ........................................................ A61C 3/00
[52] U.S. Cl. ........................................................ 433/3; 433/8
[58] Field of Search ................................ 433/8, 9, 10, 3, 433/24

[56] References Cited

U.S. PATENT DOCUMENTS

| | | |
|---|---|---|
| 1,919,762 | 9/1931 | Aderer. |
| 3,686,762 | 8/1972 | Sutter ............................. 433/3 |
| 3,871,098 | 3/1975 | Dean .............................. 433/3 |
| 4,626,208 | 12/1986 | Hall ............................... 433/3 |
| 4,659,309 | 4/1987 | Merkel ........................... 433/9 |
| 4,913,653 | 4/1990 | Bolliger et al. ............... 433/3 |
| 4,952,141 | 8/1990 | Wool ............................. 433/3 |
| 5,062,794 | 11/1991 | Miura ............................ 433/8 |
| 5,064,369 | 11/1991 | Kawaguchi ................... 433/3 |
| 5,074,783 | 12/1991 | Reher ............................ 433/8 |
| 5,242,299 | 9/1993 | Yoshida ......................... 433/8 |
| 5,304,061 | 4/1994 | Nelson .......................... 433/8 |

OTHER PUBLICATIONS

Ormco Corporation 1990, sheet 1 Bondable Bracket Assemblies.
Ormco Corporation 1990, sheet 2 "The Mini :Wick" System.
Ormco Corporation 1990, sheet 3 ETM–Bonding Bonding & Banding.

*Primary Examiner*—Cary E. O'Connor
*Attorney, Agent, or Firm*—Dowell & Dowell

[57] ABSTRACT

An orthodontic bracket having a base with a front face and spaced tie wings, with a generally central recess provided between the tie wings. With non-metal brackets, a separate jig or insert may be positioned between the tie wings. The jig or insert includes a central recess. The orthodontic brackets are designed to be positioned on an individual's tooth with the aid of a conventional bracket positioning gauge having a guide which is received in the recess of a bracket or the recess of a jig or insert. In alternate embodiments, one or more grooves may be provided between the tie wings to both assist in bracket positioning and to reduce friction between a bracket and the archwire which extends between brackets.

11 Claims, 2 Drawing Sheets

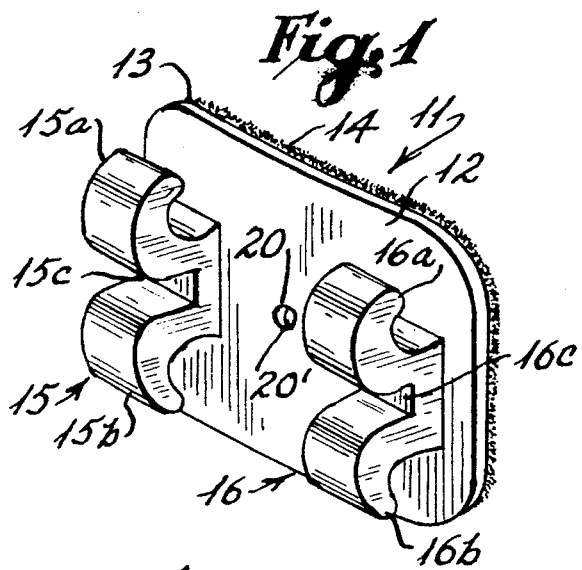
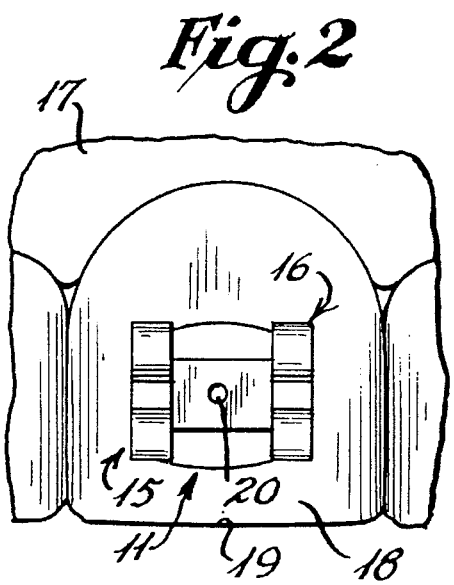
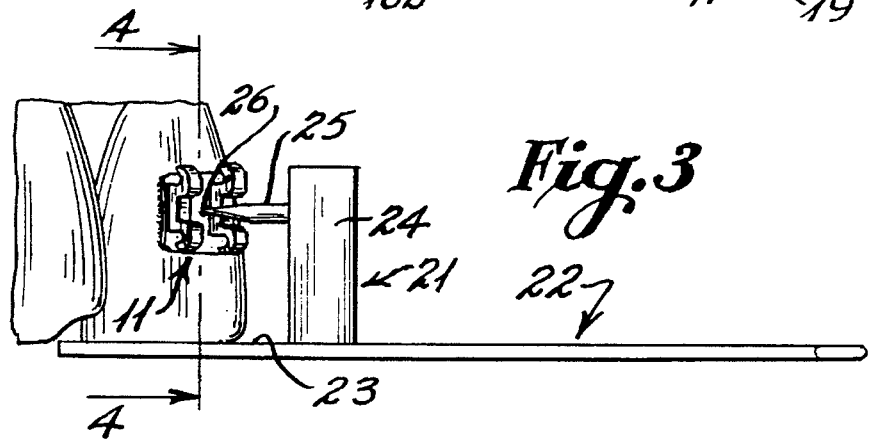
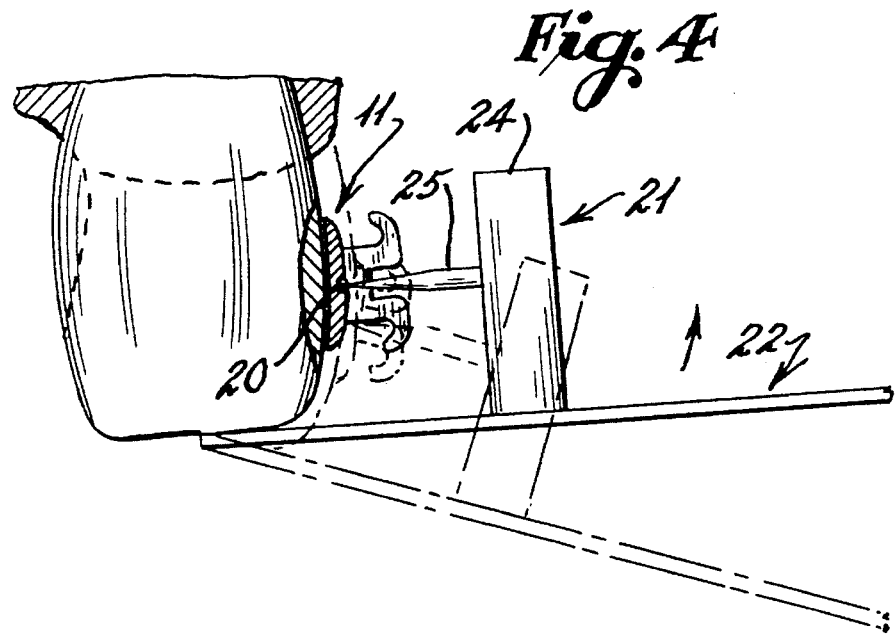

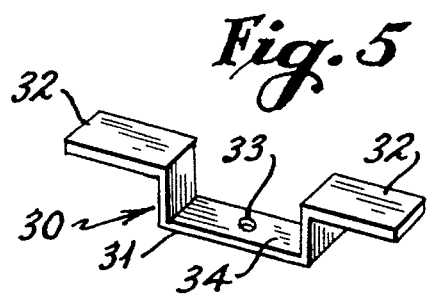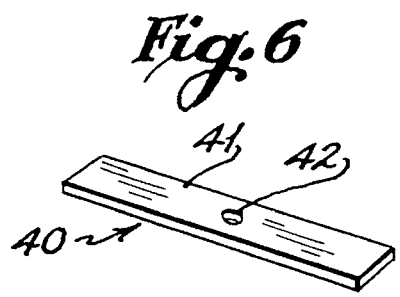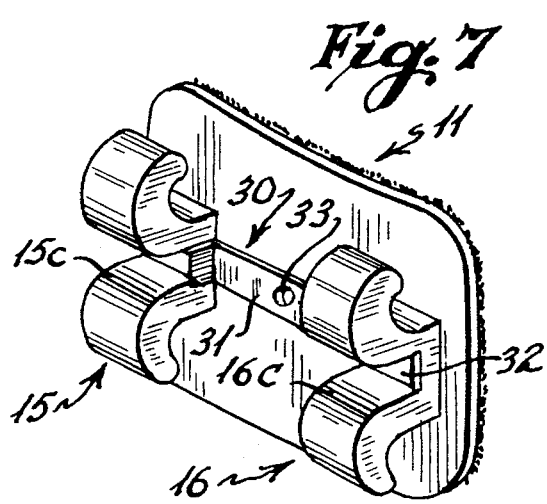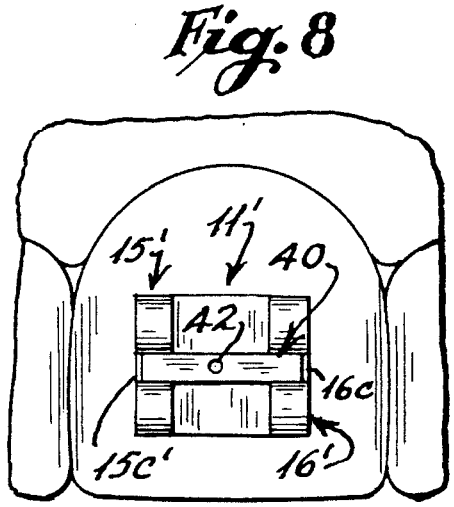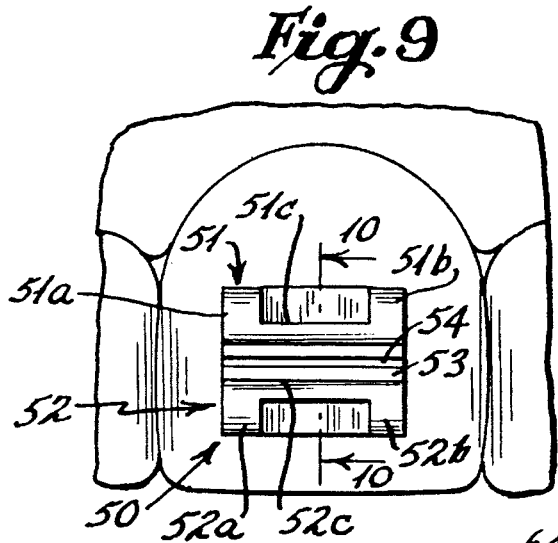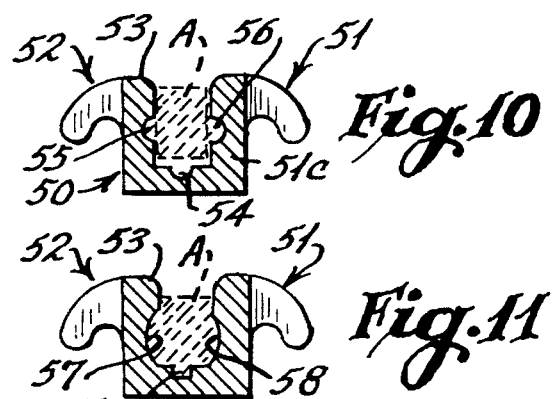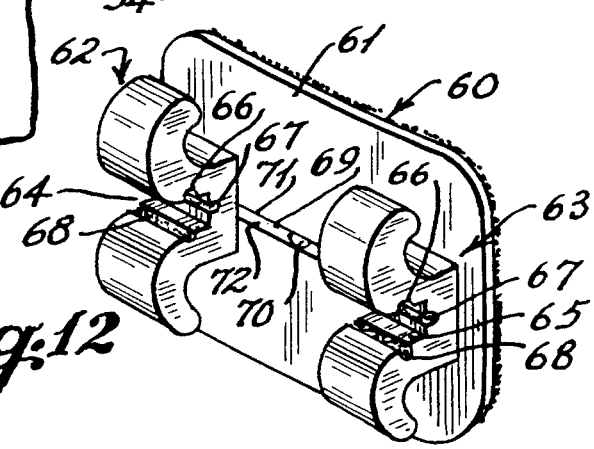

ORTHODONTIC BRACKETS

This application is a continuation of application Ser. No. 08/172,236, filed Dec. 23, 1993 now abandoned.

BACKGROUND OF THE INVENTION

1. Field of the Invention

The invention relates to the field of orthodontics, and, more particularly, to orthodontic brackets that can be consistently, precisely positioned at predetermined locations on teeth with the aid of a conventional bracket positioning gauge. The brackets of the present invention include a central recess for receiving the tip of the positioning gauge. In an alternate embodiment, separate jigs or inserts having a recess therein are placed between the tie wings of a bracket.

In further embodiments, one or more grooves may be provided in the face of a bracket between the tie wings to both assist in bracket positioning and to reduce friction between the bracket and an archwire.

2. History of the Related Art

The goal of orthodontic treatments is to achieve the correct alignment of all of the teeth and a proper occlusion so that the opposing surfaces of the upper and lower teeth properly contact each other when an individual bites. When this goal is realized, an individual is assured of having more uniform tooth wear, healthier teeth and gums, and an attractive smile.

It has not been heretofore possible, however, to achieve a correct teeth alignment and occlusion for all individuals because of the great difficulty experienced by orthodontists attempting to precisely position orthodontic brackets on patients' teeth even with the aid of bracket positioning guides. Consequently, misalignments of the teeth and malocclusions have resulted despite individuals having endured oftentimes lengthy and painful orthodontic treatments.

Precise positioning of orthodontic brackets at proper locations on the teeth avoids a number of problems that otherwise would occur. Orthodontic brackets and their associated archwires control the ultimate arrangement of the teeth. Thus, proper placement of the orthodontic brackets is critical for achieving a successful orthodontic treatment.

Regarding orthodontic bracket positioning, if a bracket is positioned too high on a tooth relative to its bottom (incisal or occlusal) surface, the force exerted by the attached archwire will pull the tooth too far downward and produce an excessive tooth length. Consequently, a malocclusion will result and the individual's bite will be unsatisfactory.

Similarly, if an orthodontic bracket is positioned too low on a tooth, the tooth will be pushed too far upward by the archwire and the resulting tooth length will be inadequate, also causing a malocclusion. Accordingly, correct vertical placement of orthodontic brackets is mandatory to achieve a proper occlusion.

It is also necessary to correctly horizontally position orthodontic brackets on the teeth to achieve a successful orthodontic treatment. That is, if an orthodontic bracket is located excessively horizontally off-center, the associated tooth is twisted by the forces imparted on the bracket by the archwire. Consequently, the teeth are misaligned.

Improper orthodontic bracket placement on the teeth causes the orthodontic treatment to be unnecessarily prolonged. This is because brackets which are improperly positioned must be subsequently repositioned. Alternatively, instead of repositioning improperly positioned brackets, bends are sometimes formed in the archwire to compensate for any misalignment which would otherwise occur. Such measures are unsatisfactory, however, because additional stresses are placed on the brackets that may cause the bracket to become loose or even separate from the teeth, not to mention the additional pain and suffering to a patient.

Accordingly, proper orthodontic bracket placement reduces treatment costs because the need for bracket repositioning and replacement is eliminated.

Also, proper bracket placement reduces patient discomfort as the number of oftentimes painful and traumatic visits to the orthodontist are minimized because the teeth reach their ultimate proper arrangement in a shorter period of time.

In addition to proper bracket placement, improper archwire control between an archwire and a bracket can often increase the period of patient treatment. During the early stages of treatment, it is preferred to permit a somewhat free movement between an archwire and a bracket so that the teeth are not restrained from corrective movement. Therefore, if too much friction is created between brackets and archwires, a resistance to tooth realignment is created. Thus, the decreased resistance results in a more rapid and less painful orthodontic treatment.

In view of the undesirable problems associated with improper orthodontic bracket placement, there has been a need for an orthodontic bracket which can be consistently, precisely positioned on the teeth so as to avoid the problems of misalignment and malocclusion that are associated with the known orthodontic brackets.

Further, there exists a need to selectively control the resistance created between orthodontic brackets and archwires to permit rapid tooth alignment during early stages of treatment and more controlled alignment during latter stages of treatment.

SUMMARY OF THE INVENTION

The present invention has been made in view of the above-described inadequacies of the related art and has as an object to provide orthodontic brackets that facilitate consistent and precise positioning on teeth and thus enable a more accurate method of bracket placement than had been previously possible. The present invention enables the known problems associated with the improper positioning of orthodontic brackets to be avoided.

The present invention also facilitates the control of tooth realignment during patient treatment by permitting frictional forces between brackets and archwires to be reduced.

Additional objects and advantages of the present invention will become apparent from the detailed description which follows, considered in conjunction with the accompanying drawing figures.

To achieve the objects of the invention, in the preferred embodiment, the orthodontic bracket comprises a base having a front face with a recess formed preferably approximately at its center. The recess is formed in the front face of the orthodontic bracket to provide a fixed reference point and to facilitate simple and precise horizontal and vertical placement of the bracket with the aid of a conventional bracket positioning gauge. As opposed to a recess or opening, or in addition thereto, in some embodiments, a groove may be provided between the tie wings of a bracket to further facilitate precise bracket placement.

In a first alternate embodiment, and especially for use with non-metallic brackets, a separate plastic or metallic jig or insert having a central recess therein may be placed on the front face of a bracket with the ends thereof seated within or intermediate the generally U-shaped tie wings of such brackets. In this manner, pre-existing brackets without central recesses may be accurately horizontally and vertically positioned. With clear brackets, the central recess may be colored so as to be readily apparent to the practitioner.

In a second alternate embodiment, one or more grooves may be provided in the front face of a bracket which extend between the tie wings. The grooves are provided, not only to permit a reference line for alignment of the bracket using associated positioning gauges, but also to decrease the contact area between a bracket and an archwire to thereby reduce frictional resistance to permit a relative free movement therebetween. The relative free movement allows teeth to be brought more rapidly toward a proper position during early stages of patient treatment.

BRIEF DESCRIPTION OF THE DRAWINGS

In the accompanying drawings:

FIG. 1 is a perspective view of an orthodontic bracket in accordance with a preferred embodiment of the present invention;

FIG. 2 is a front illustrational view of the orthodontic bracket of FIG. 1 positioned on an individual's tooth;

FIG. 3 is a front illustrational view depicting the manner of positioning the orthodontic bracket of FIG. 1 on an individual's tooth with the aid of a bracket placement tool; and FIG. 4 is a side illustrational view taken in the direction of line 4—4 of FIG. 3 and further depicting in dotted lines positional adjustment of the orthodontic bracket.

FIG. 5 is a perspective view of a first form of alignment jig which may be used with existing orthodontic brackets to provide a central recess for horizontal and vertical alignment purposes.

FIG. 6 is a perspective view of a second form of alignment jig which may be used with existing orthodontic brackets to provide a central recess for horizontal and vertical alignment purposes.

FIG. 7 is a perspective illustrational view of the alignment jig of FIG. 5 mounted along the front face and between the tie wings of a first type conventional orthodontic bracket.

FIG. 8 is a front elevational view of the alignment jig of FIG. 6 mounted along the front face and between the tie wings of a second type conventional orthodontic bracket.

FIG. 9 is a front elevational view of an alternate embodiment of the present invention showing an alignment groove extending along the archwire guide slot between two reinforced tie wings of an orthodontic bracket.

FIG. 10 is an enlarged cross-sectional view taken along line 10—10 of FIG. 9 showing an archwire in dotted lines.

FIG. 11 is an enlarged cross-sectional view of another embodiment of orthodontic bracket similar to that of FIG. 9 taken alone line 10—10 of FIG. 9.

FIG. 12 is a perspective view of another embodiment of orthodontic bracket incorporating features of previous embodiments of the present invention.

DETAILED DESCRIPTION OF THE PREFERRED EMBODIMENT

With reference to the drawing figures, FIG. 1 illustrates a preferred embodiment of the orthodontic bracket in accordance with the present invention. The orthodontic bracket comprises a base 11 having a front face 12 and a back face 13. The back face is appropriately concave so that it conforms to the contour of the front surface of an individual's tooth. A pad 14 is attached to the back face 13. Adhesive for bonding the orthodontic bracket to a tooth is applied to the pad.

A pair of spaced ligating or tie wings 15 and 16 extend from the front face 12. The tie wings have two pairs of tie wing ears 15a, 15b; 16a, 16b; and slots 15c and 16c, respectively. As illustrated in FIG. 2, the tie wing ears 15a, 16a are closest to an individual's gums 17 when the orthodontic bracket is fixed to tooth 18 and are known as gingival tie wing ears, and the tie wing ears 15b, 16b closest to the bottom edge 19 of the tooth are known as the incisal or occlusal tie wing ears depending on the type of tooth.

The slots 15c and 16c are substantially aligned with respect to each other to receive an arch wire (not shown) which extends laterally of the bracket 10 in both directions and connects the bracket to the orthodontic brackets on contiguous teeth. A conventional elastic band (not shown) composed of an elastic or non-elastic material is engaged by the tie wing ears and surrounds the arch wire to retain it in the slots 15c and 16c.

In accordance with the present invention, the front face 12 of the base 11 includes a contained recess 20 formed with a surrounding side wall 20' which may be round in shape, as shown in FIGS. 1 and 2, located intermediate the tie wings 15 and 16 and preferably approximately at the center of the front face. The recess provides a reference point and facilitates precise placement of the orthodontic bracket at a predetermined location on the front face of an individual's tooth as will be described in greater detail below.

FIGS. 3 and 4 illustrate positioning of the orthodontic bracket 10 on the front surface of tooth 14 with the aid of a conventional bracket positioning gauge 21. The positioning gauge includes a plurality of arms such as arm 22 having an edge 23 which contacts the lower occlusal or incisal surface 19 of the tooth during placement of the bracket. The arms of the positioning gauge each provide a different positional setting for an orthodontic bracket. A post 24 extends from the arm 22 and a shaft 25 is connected to the post and extends substantially parallel relative to the arm. A tip 26 is formed at the end of the shaft remote from the block. The vertical distance from the edge 23 to the center of the shaft is different for each of the arms. For conventional bracket positioning gauges having four arms, this distance is fixed for each of the four arms and may be, for example, 3.5 mm, 4.0 mm, 4.5 mm and 5.0 mm.

The edge 23 of the arm 22 is approximately parallel to the surface 19 of the tooth 18 when the bracket positioning gauge is oriented as depicted in FIG. 3 and in solid lines in FIG. 4. At this orientation, the distance between the tip of the positioning gauge and the tooth surface 19 is approximately equivalent to the distance between the tip and the face 22 of the tool. Thus, using a selected arm of the positioning gauge, the orthodontic bracket can be placed at a known distance from the incisal or occlusal surface of the tooth. For example, to place the orthodontic brackets about 4.0 mm from the tooth surface 19, the arm of the placement tool having a distance of 4.0 mm from its tip 26 to its edge 23 is selected.

The orthodontic brackets can be placed at positions on the individual's tooth other than the position illustrated in FIG. 3. As depicted in dotted lines in FIG. 4, the orthodontic bracket can be positioned at relatively lower positions on the tooth by rotating the positioning gauge in a clockwise direction. The positioning gauge can similarly be rotated in a counter-clockwise direction to place the orthodontic bracket at a relatively higher position on the tooth than illustrated in FIG. 3.

A method of positioning an orthodontic bracket in accordance with a preferred embodiment of the present invention with the aid of a conventional bracket positioning gauge will now be described.

Initially, unless and adhesive has been pre-applied, an adhesive is applied to the pad 13 on the back face of the orthodontic bracket 10. The adhesive is preferably a light curing type so that a controlled curing rate is achieved that can be closely monitored to allow adequate time for positioning the bracket before a bond is initiated.

Next, the pad is placed in contact with the front surface of a tooth at an estimated horizontal and vertical position by employing a hand instrument designed for this purpose. The estimated position is preferably as close as possible to the ultimate predetermined or desired position for the bracket. The orthodontic bracket is gently pressed against the tooth to expel excess adhesive, which is removed using an appropriate tool.

The bracket positioning gauge is then employed to precisely vertically and horizontally position the orthodontic bracket at the predetermined position. The arm of the positioning gauge having the desired fixed height setting for the tip 26 is selected for this purpose.

The remote portion of edge 23 of the arm is brought into contact with the lower tooth surface 19 and the tip 26 of the shaft 25 is moved until it is loosely received in the recess 20 of the orthodontic bracket. The positioning gauge is then adjusted until it reaches the desired position as illustrated in FIG. 3 in which the arm 22 is substantially parallel to the tooth lower surface 19. In this position, the recess is at a distance from the tooth surface 19 approximately equal to the known distance from the tip 26 to the edge 23 of the arm of the positioning gauge. To remove the positioning gauge, the tip is moved out of the recess 20 and the edge 23 is moved away from the tooth surface 19.

After the orthodontic bracket is positioned at the predetermined location, the hand instrument is used to urge the bracket to firmly seat the bracket against the tooth, thus expelling any excess adhesive. Finally, the adhesive is cured to establish a bond between the bracket and tooth by directing a light source at the tooth-bracket interface. It should be noted that self cure adhesives may also be used to effect bonding of the brackets.

With particular reference to FIGS. 5–8, two additional embodiments of the present invention are disclosed in greater detail. In the preferred embodiment, the recess is formed directly in the front face of the orthodontic bracket. In some instances, and especially with non-metallic brackets, if a recess is provided in the front face, it may be difficult for the practitioner to actually see the recess. Therefore, it is preferred in the use of such brackets to provide some type of coloring material in the area of the recess or surrounding the recess to make the recess visually apparent. This can be done by providing a dye or food coloring which is applied to the area of the recess.

As a further alternative, and in order to allow the teachings of the present invention to be utilized with existing conventional metallic or non-metallic brackets, separate jigs or inserts may be provided which incorporate a central recess. With specific reference to FIG. 5, a first type of jig or insert 30 is shown formed of a strip of plastic or metal material having a central generally U-shaped portion 31 and side extensions 32. A recess 33 is formed centrally in the front face 34 of the central portion. The jig or insert 30 may be colored to make it easy to identify and locate the recess 33, especially if the insert is to be used with clear orthodontic brackets. In some instances, the recess 33 may be an opening through the jig.

With specific reference to FIG. 7, the jig or insert of FIG. 5 is shown as being placed on an orthodontic bracket 11. The jig is placed so that the extensions 32 are seated within the slots 15c and 16c of the tie wings 15 and 16. As shown, the width of the jig 30 is substantially identical to the width of the slots 15c and 16c and the width of the central portion 31 is substantially equal to the distance between the tie wings 15 and 16. In this manner, when the insert is mounted in place, the recess 33 therein will be positioned centrally of the front face of the bracket 11 and functions as the recess 20 disclosed in the previous embodiment to receive the tip 26 of a positioning gauge. In addition to the horizontal placement shown, the jig may also be used in a vertical manner in/on the bracket to achieve proper alignment. In the use of the jig, once the bracket has been properly aligned and the adhesive cured, thereby bonding the bracket in position, the jig is simply lifted from its engagement with the bracket.

A further embodiment of the present invention is shown in FIG. 6 as including a generally rectangular jig 40 having an upper surface 41 in which is formed a recess or opening 42. The recess or opening 42 is provided generally centrally of the insert or jig 40. This jig is utilized with brackets having tie wings with slots formed therein which are substantially flush with the upper surface of the orthodontic bracket. With specific reference to FIG. 8, a bracket 11' of this type is shown having tie wings 15' and 16' which include generally flush slot 15c' and 16c'. The insert 40 is shown as being of a width to be cooperatively seated within the grooves 15c' and 16c' and is thereby retained in position when seated flush against the face of the bracket 11'. As with the previous embodiment, once the insert 40 has been utilized to properly position the bracket, the insert may be removed from the bracket for further use.

Again, either of the jigs or inserts 30 or 40 may be constructed of metallic or plastic material and either may be appropriately colored to facilitate their use with clear orthodontic brackets. In some instances, the jigs 30 and 40 may have slightly arcuate rear surfaces so as to conform to orthodontic brackets having curved outer faces.

Another type of orthodontic bracket is shown in FIG. 9 at 50. With this bracket, the tie wings 51 and 52 are disposed along the entire length of the bracket and define an archwire slot 53 therebetween. Each tie wing includes a pair of spaced wing ears 51a and 51b and 62a and 62b which are integrally connected by reinforcing walls 51c and 52c.

In this embodiment, as opposed to forming a recess centrally of the archwire slot 53, and as opposed to utilizing a separate insert, an elongated groove 54 is provided which extends along the length of the archwire slot. In this embodiment, the tip 26 of the positioning gauge may be inserted within the groove 54 and the bracket 50 positioned in a manner similar to that discussed with respect to the embodiment disclosed in FIGS. 1–4.

In the present embodiment, the groove 54 not only provides a recessed area for receiving the tip of the positioning gauge 21, but the groove 54 may be associated with other grooves in order to reduce the contact area between the bracket and an archwire "A" extending therethrough. With particular reference to FIGS. 10 and 11, several variations of the present embodiment are shown in greater detail. In FIG.

10, there is shown a cross-section of the orthodontic bracket shown in FIG. 9 which includes the groove 54 which extends along the length of the archwire slot 53. The archwire is shown in dotted line seated within the archwire slot. In order to reduce the frictional resistance between the archwire "A" and the walls of the archwire slot 53, additional elongated recesses or grooves 55 and 56 are made in opposing walls of the tie wings 51 and 52 and the associated reinforcing walls 51c and 52c. Because of the longitudinally extending grooves 54, 55 and 56, the area of contact between the bracket and the archwire "A" is reduced significantly. This reduces the amount of frictional engagement between the archwire and the bracket when an archwire is placed within the archwire slot 53. During initial patient treatment, it is often preferred to allow teeth to be realigned as quickly as possible toward their final proper position. In conventional orthodontic brackets, the frictional resistance between the brackets and the archwires can retard the rate at which a tooth will move due to the binding between the bracket attached to the tooth and the archwire. By reducing the contact area between the archwire and the bracket, a significant reduction in frictional resistance is achieved, thereby allowing the bracket to slide relative to the archwire to permit a more rapid alignment of teeth being treated.

With respect to FIG. 11, a slight variation of the structure shown in FIG. 10 is disclosed. In this variation, as opposed to having well-defined grooves 55 and 56 extending longitudinally of the archwire slot, the sides of the archwire slot are formed as opposing arcuate sections 57 and 58. With this structure, an even greater reduction in frictional resistance is achieved between the archwire "A" and the bracket.

With specific reference to FIG. 12, another embodiment of the present invention is disclosed in greater detail. In the embodiment of the invention of FIG. 12, the orthodontic bracket 60 embodies characteristics of each of the embodiments disclosed in FIGS. 1–4 and 9–11. The bracket 60 includes a front face 61 from which extend a pair of tie wings 62 and 63 having tie wing slots 64 and 65 defined thereby, respectively. In order to reduce the frictional engagement of an archwire extending through the archwire slot 64 and 65, one or more grooves such as shown at 66, 67 and 68 are formed in each of the tie wings so as to form a configuration similar to that disclosed in cross-section in FIG. 10. In a similar manner, the archwire slots 64 and 65 could be formed having a configuration more similar to that disclosed in FIG. 11. In this manner, frictional resistance is reduced significantly between an archwire and the archwire tie wings.

In addition to reducing the resistance between an archwire and the tie wings of the present embodiment, an alignment groove 69 defined by opposing side walls 71 and 72 extends between the tie wings 62 and 63 and is aligned generally centrally of the bracket and with the tie wing slots 64 and 65. A centralized recess 70 is made within the slot 69 to serve as a central locator point for receiving the tip 26 of an alignment gauge as has previously been discussed. In view of the foregoing, the bracket 60 offers several advantages over existing conventional orthodontic brackets.

It should be noted that the use of an elongated groove such as 69 may be incorporated into the embodiments of the invention disclosed in FIGS. 1–8 so the combinations of recesses and grooves, grooves alone, and recesses alone may be utilized in accordance with the teachings of the present invention, both with orthodontic brackets and with jigs for positioning orthodontic brackets as set forth hereinabove.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims, and their equivalents.

What is claimed is:

1. An orthodontic bracket can be moved into a desired position on the front surface of a tooth using a bracket positioning means having a tip, said bracket comprising, a base including a front face and a rear surface, a contained recess formed with a surrounding wall in said front face, said contained recess being of a size and shape to cooperatively receive the tip of the bracket positioning means therein such that the tip is engageable with said surrounding wall, whereby the tip of the bracket positioning means can be received within said contained recess for moving said bracket vertically into the desired position on the front surface of the tooth, a pair of spaced tie wings extending from said front face of said base on either side of said contained recess, said tie wings defining at least one archwire slot, a groove formed in said front face and extending between said tie wings, said groove having opposing side walls which are spaced to cooperatively receive the tip of the positioning means therebetween so that the tip can be received with said groove for moving said bracket vertically into the desired position on the front surface of a tooth.

2. The orthodontic bracket of claim 1, wherein said contained recess is located generally equidistant intermediate said first and second tie wings and within said groove.

3. The orthodontic bracket of claim 1, including at least one groove formed in said at least one archwire slot for reducing frictional contact area between an archwire and the orthodontic bracket.

4. The orthodontic bracket of claim 3, including a plurality of spaced grooves in said at least one archwire slot.

5. The orthodontic bracket of claim 3, in which said at least one archwire slot has opposing generally arcuate wall portions.

6. A combination of orthodontic bracket and alignment jig comprising:

an orthodontic bracket having a front face and a rear surface, tie wings extending from said front face in spaced relationship to one another, a slot defined by each of said tie wings;

an alignment jig having front and rear surfaces, a central portion and opposite end portions, a contained recess formed by a surrounding side wall in said central portion; and said alignment jig being mounted against said front face of the bracket in alignment with said slots of said tie wings.

7. The combination of claim 6, in which said recess is formed as an opening through said alignment jig.

8. The combination of claim 6, in which said central portion is generally U-shaped.

9. A device for use in aligning orthodontic brackets, wherein the brackets have an outer face and an inner surface and tie wings extending in spaced relationship with respect to one another from the outer face and wherein the tie wings define an open slot, the alignment device comprising a jig means having a front and rear surface, a central portion and opposite end portions, a contained recess formed by a surrounding size wall in said central portion, and at least one of said central and said end portions being of a size to be cooperatively received within the slots formed by the tie wings of the orthodontic bracket, whereby when said jig means is positioned on an orthodontic bracket with a portion thereof within the slots, the recess in said central portion will be positioned intermediate the tie wings.

10. The device of claim 9, in which said recess is formed as an opening through said jig means.

11. The device of claim 10, in which said central portion is generally U-shaped.

* * * * *